(12) United States Patent
Ueda et al.

(10) Patent No.: US 11,800,643 B2
(45) Date of Patent: **\*Oct. 24, 2023**

(54) DEVICE HAVING CLOSED SPACE BETWEEN OVERLAPPING SEALING MEMBERS

(71) Applicant: Japan Aviation Electronics Industry, Limited, Tokyo (JP)

(72) Inventors: Shinji Ueda, Tokyo (JP); Osamu Hashiguchi, Tokyo (JP)

(73) Assignee: JAPAN AVIATION ELECTRONICS INDUSTRY, LIMITED, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/700,747

(22) Filed: Mar. 22, 2022

(65) Prior Publication Data
US 2022/0319938 A1    Oct. 6, 2022

(30) Foreign Application Priority Data

Apr. 5, 2021  (JP) .................................. 2021-064367
Jan. 21, 2022 (JP) .................................. 2022-008089

(51) Int. Cl.
*H05K 1/14* (2006.01)

(52) U.S. Cl.
CPC .................................. *H05K 1/144* (2013.01)

(58) Field of Classification Search
CPC .... H05K 5/069; H05K 1/0298; H05K 9/0043; H05K 1/144; H05K 5/068; H01M 50/178;
(Continued)

(56) References Cited

U.S. PATENT DOCUMENTS

| 5,000,256 A | 3/1991 | Tousignant |
| 5,285,619 A | 2/1994 | Jones |
| 5,403,973 A | 4/1995 | Santilli et al. |
| 5,406,945 A * | 4/1995 | Riazzi ..................... A61B 5/25 600/394 |

(Continued)

FOREIGN PATENT DOCUMENTS

| JP | H08-235935 A | 9/1996 |
| JP | H11-126037 A | 5/1999 |

(Continued)

OTHER PUBLICATIONS

Extended European Search Report in EP 22165011.2-1212, dated Sep. 26, 2022.

(Continued)

*Primary Examiner* — James Wu
(74) *Attorney, Agent, or Firm* — Collard & Roe, P.C.

(57) ABSTRACT

A device includes a first sealing member, a second sealing member, a first circuit member and a second circuit member. The first sealing member includes, as a base thereof, a first film formed of a film and includes a conductive portion made of conductor. The device is formed with a closed space. The closed space is enclosed by the first sealing member and the second sealing member and is shut off from an outer space located outside the device. The first circuit member and the second circuit member are shut in the closed space and include a first contact point and a second contact point, respectively. At least one of the first circuit member and the second circuit member includes an electrode. The conductive portion is in contact with the electrode in the closed space and is partially exposed to the outer space located outside the device.

8 Claims, 9 Drawing Sheets

(58) Field of Classification Search
CPC ....... A61B 5/024; H01L 23/10; H01L 23/043; H01L 23/045
See application file for complete search history.

(56) References Cited

U.S. PATENT DOCUMENTS

| | | | |
|---|---|---|---|
| 5,689,878 | A | 11/1997 | Dahringer et al. |
| 3,044,415 | A1 | 10/2011 | Messere et al. |
| 9,770,182 | B2 * | 9/2017 | Bly .................. A61B 5/259 |
| 2009/0022949 | A1 | 1/2009 | Horita et al. |
| 2009/0076363 | A1 | 3/2009 | Bly et al. |
| 2019/0287892 | A1 * | 9/2019 | Sääski .................. H05K 3/4644 |
| 2021/0020528 | A1 | 1/2021 | Meier et al. |
| 2022/0192043 | A1 * | 6/2022 | Ueda .................. H05K 5/0095 |
| 2022/0322518 | A1 * | 10/2022 | Ueda .................. H01L 23/293 |

FOREIGN PATENT DOCUMENTS

| | | |
|---|---|---|
| JP | 2000-173394 A | 6/2000 |
| JP | 2001-332654 A | 11/2001 |
| JP | 2004-119559 A | 4/2004 |
| JP | 2004-342967 A | 12/2004 |
| JP | 2006-024054 A | 1/2006 |
| JP | 2007-235045 A | 9/2007 |
| JP | 2009-512977 A | 3/2009 |
| JP | 2015-019020 A | 1/2015 |
| JP | 2018-106796 A | 7/2018 |

OTHER PUBLICATIONS

Extended European Search Report in EP 22165018.7 -1212, dated Sep. 27, 2022.

* cited by examiner

DEVICE HAVING CLOSED SPACE BETWEEN OVERLAPPING SEALING MEMBERS

CROSS REFERENCE TO RELATED APPLICATIONS

This application is based on and claims priority under 35 U.S.C. § 119 to Japanese Patent Applications No. JP 2021-064367 filed Apr. 5, 2021, and No. JP 2022-008089 filed Jan. 21, 2022, the contents of which are incorporated herein in their entirety by reference.

BACKGROUND OF THE INVENTION

This invention relates to a device comprising a circuit member sealed by a film.

For example, a device which can be made thinner is disclosed in JP2001-332654A (Patent Document 1), the content of which is incorporated herein by reference.

Figure 17:
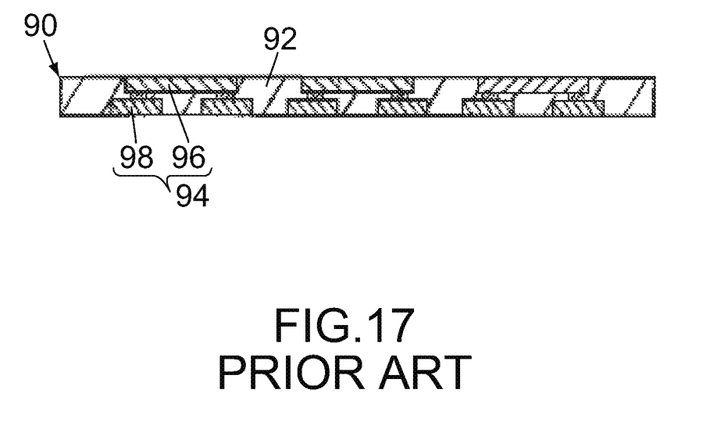
FIG. 17 is a cross-sectional view showing a device of Patent Document 1.

Referring to FIG. 17, Patent Document 1 discloses a module (device) 90 with built-in semiconductor chips. The device 90 comprises a thermosetting resin composition (sealing resin) 92 and a circuit member 94 including semiconductor chips 96 and wiring patterns 98. The sealing resin 92 is formed so that the circuit member 94 is embedded therewithin. Then, a surface of the sealing resin 92 is polished so that the device 90 is made thinner.

Further reduction in thickness is required for a device comprising a circuit member.

SUMMARY OF THE INVENTION

It is therefore an object of the present invention to provide a new device which can be made thinner.

An aspect of the present invention provides a device comprising a first sealing member, a second sealing member, a first circuit member and a second circuit member. The first sealing member comprises, as a base of the first sealing member, a first film formed of a film and comprises a conductive portion made of conductor. The device is formed with a closed space. The closed space is enclosed by the first sealing member and the second sealing member and is shut off from an outer space located outside the device. The first circuit member and the second circuit member are shut in the closed space. The first circuit member comprises a first contact point. The second circuit member comprises a second contact point. The first contact point and the second contact point are pressed against each other to be in contact with each other in the closed space. At least one of the first circuit member and the second circuit member comprises an electrode. The conductive portion is in contact with the electrode in the closed space and is partially exposed to the outer space located outside the device.

Another aspect of the present invention provides a device comprising a first sealing member, a second sealing member, a first circuit member and a second circuit member. The first sealing member comprises, as a base of the first sealing member, a first film formed of a film and comprises a conductive gel. The device is formed with a closed space. The closed space is enclosed by the first sealing member and the second sealing member and is shut off from an outer space located outside the device. The first circuit member and the second circuit member are shut in the closed space. The first circuit member comprises a first contact point. The second circuit member comprises a second contact point. The first contact point and the second contact point are pressed against each other to be in contact with each other in the closed space. At least one of the first circuit member and the second circuit member comprises an electrode. The conductive gel comprises a conductive portion. The conductive portion is in contact with the electrode in the closed space and is partially exposed to the outer space located outside the device.

According to the device of an aspect of the present invention, the first sealing member and the second sealing member overlap with each other while the first circuit member and the second circuit member (hereafter, simply referred to as "circuit members") are sandwiched therebetween. The first sealing member is basically formed of a film. Moreover, the structure of each of the circuit members is not restricted except that the circuit members should be provided with the contact points and the electrode. Thus, each of the circuit members of an aspect of the present invention has a simple structure and can be formed of various material. For example, each of the circuit members may be an insulation film formed with a conductive pattern having the contact point and the electrode. In this instance, the thickness of the entire device can be made extremely thin. Thus, an aspect of the present invention provides a new device which can be made thinner.

An appreciation of the objectives of the present invention and a more complete understanding of its structure may be had by studying the following description of the preferred embodiment and by referring to the accompanying drawings.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION

Figure 1:
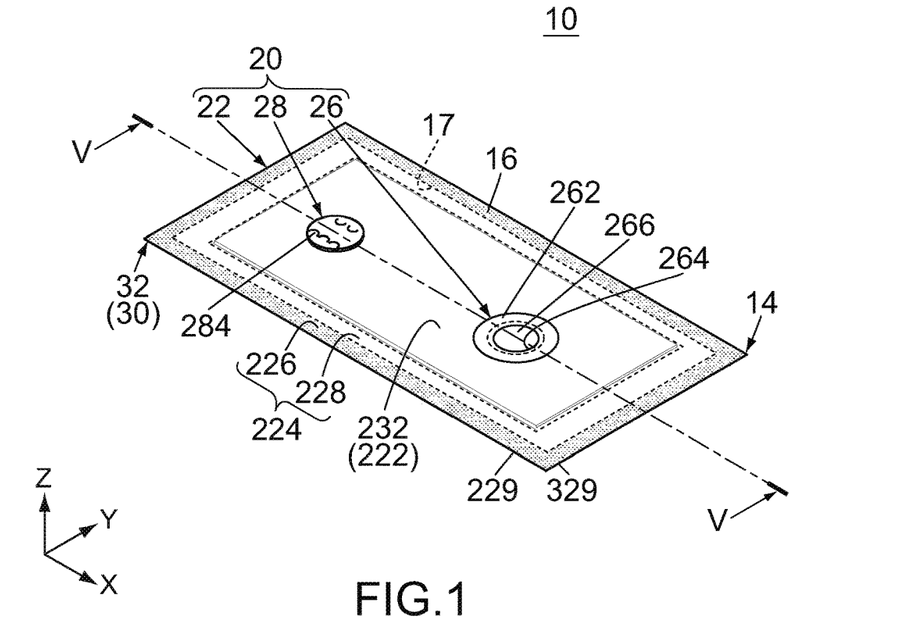
FIG. 1 is a perspective view showing a device according to an embodiment of the present invention, wherein an outline of a hidden main opening of a first film and boundary lines of a contact region formed between a first sealing member and a second sealing member are illustrated with dashed line.

Referring to FIG. 1, a device 10 according to an embodiment of the present invention is an independent electronic device. More specifically, the device 10 can work solely without another electronic device (not shown) physically attached thereto. For example, the device 10 measures the heart rate of a subject by attaching the device 10 near the heart of the subject and transmits the measurement result to another electronic device. Thus, the device 10 can be used as an electronic device for measuring biological information such as heart rate. However, the present invention is not limited thereto but is applicable to various devices having various functions.

Figure 2:
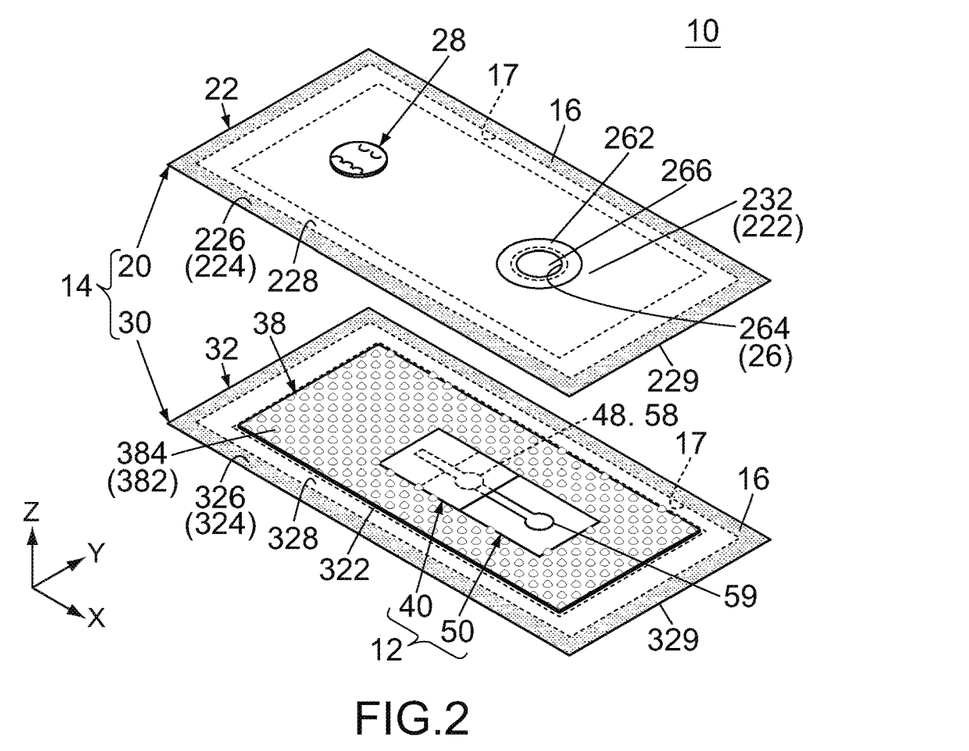
FIG. 2 is a perspective view showing the device of FIG. 1, wherein the first sealing member is removed, and an outline of the hidden main opening of the first film and boundary lines of the contact region are illustrated with dashed line.

Referring to FIG. 2 together with FIG. 1, the device 10 of the present embodiment comprises a circuit structure 12 and a sealing member 14. The circuit structure 12 is a member for enabling the device 10 to work as an electronic device. For example, the circuit structure 12 has an electronic circuit (not shown) for receiving electric signals (hereafter, referred to as "biological signals") generated from electric pulse of the heart of the subject, another electronic circuit (not shown) for measuring the electric pulse of the heart based on the received biological signals and still another electronic circuit (not shown) for transmitting the measurement result to another electronic device (not shown). The sealing member 14 entirely accommodates the circuit structure 12 therewithin and protects the circuit structure 12 from an external environment. Thus, the circuit structure 12 is shut in the sealing member 14.

Figure 8:
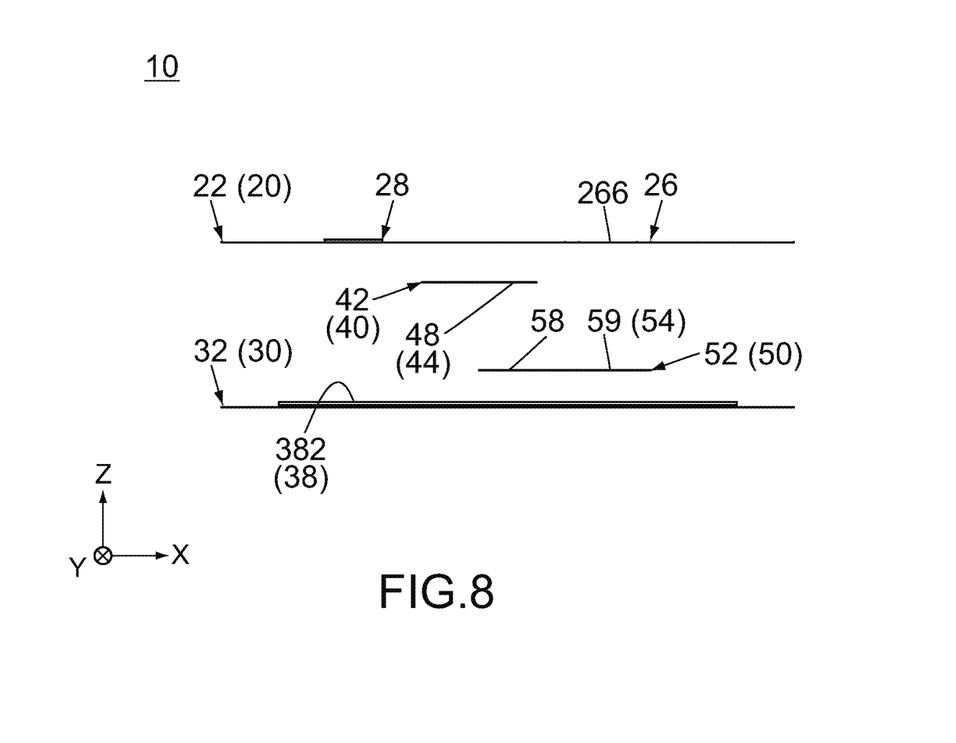
FIG. 8 is a side view showing the device of FIG. 1, wherein the device is under manufacturing process.

The circuit structure 12 of the present embodiment comprises a first circuit member 40 and a second circuit member 50. The sealing member 14 of the present embodiment comprises a first sealing member 20 and a second sealing member 30. Thus, the device 10 comprises the first sealing member 20, the second sealing member 30, the first circuit member 40 and the second circuit member 50. Referring to FIG. 8 together with FIGS. 1 and 2, the four members of the device 10, i.e., the first sealing member 20, the second sealing member 30, the first circuit member 40 and the second circuit member 50, are stacked in an upper-lower direction (Z-direction) and are combined to form the device 10 as a single structure. The device 10 of the present embodiment comprises only the aforementioned four members. However, the present invention is not limited thereto, but the device 10 may further comprise another member in addition to the aforementioned four members.

Hereafter, explanation will be made about each member of the device 10 of the present embodiment.

Figure 6:
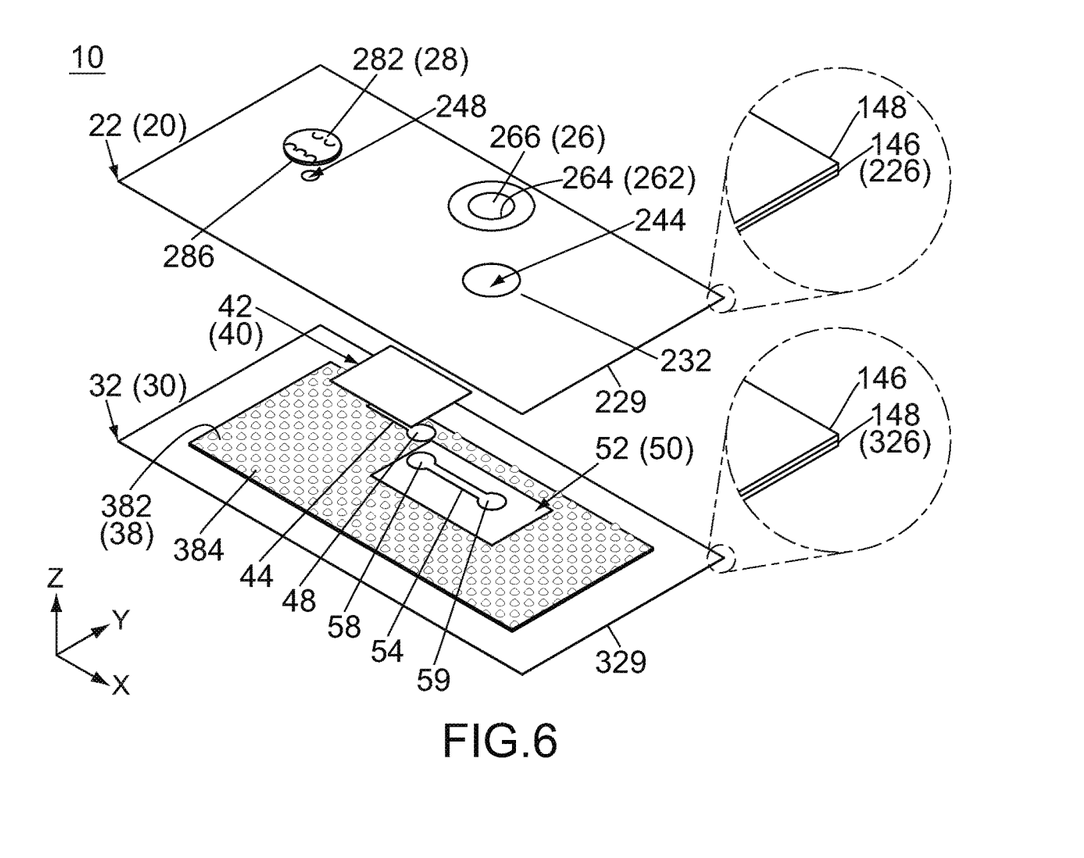
FIG. 6 is an exploded, perspective view showing the device of FIG. 1, wherein a part of the first film enclosed by dashed line and a part of a second film enclosed by dashed line are enlarged and illustrated.

Referring to FIG. 6, the first sealing member 20 of the present embodiment is formed of, as a base thereof, a first film 22 which is an insulation film. In other words, the first sealing member 20 comprises, as a base of the first sealing member 20, the first film 22 formed of a film. The first film 22 of the present embodiment is a thin, rectangular sheet and is bendable. For example, the first film 22 has a thickness of about 0.01 to 0.5 mm. The first film 22 extends in parallel to a horizontal plane (sheet plane: XY-plane). The first film 22 has a peripheral edge 229 in the XY-plane.

Figure 3:
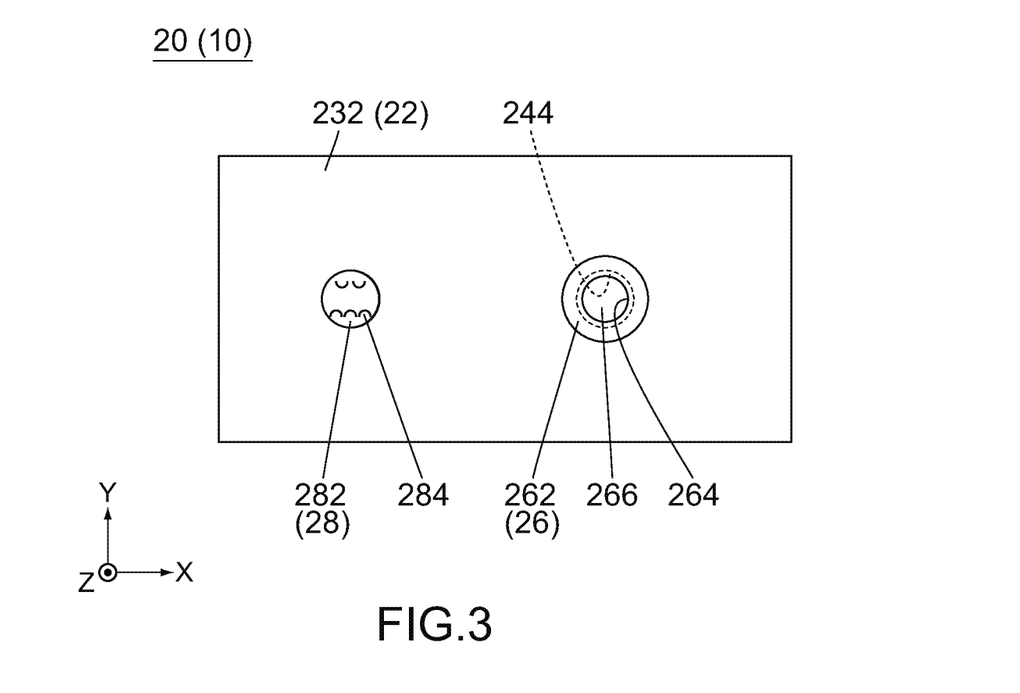
FIG. 3 is a top view showing the first sealing member of the device of FIG. 1, wherein an outline of the hidden main opening of the first film is illustrated with dashed line.
Figure 4:
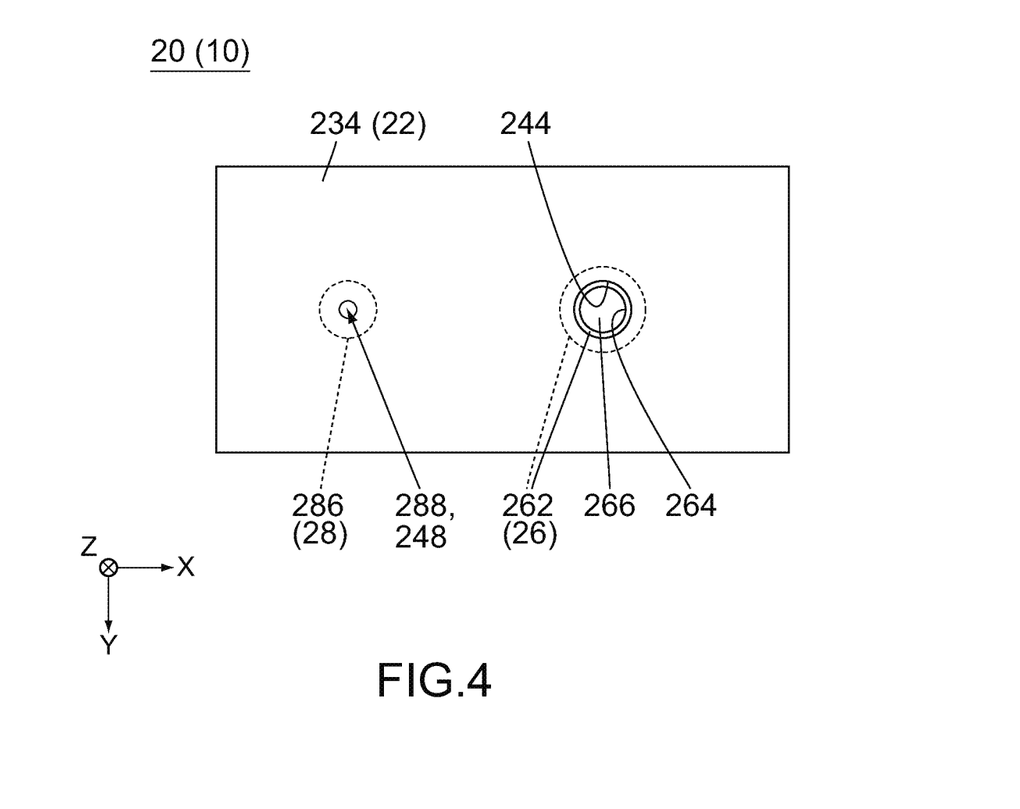
FIG. 4 is a bottom view showing the first sealing member of FIG. 3, wherein hidden outlines of a sub-member and an air valve are illustrated with dashed line.

Referring to FIGS. 3 and 4, the first film 22 has an outer surface 232 and an inner surface 234. The outer surface 232 is an upper surface (positive Z-side surface) of the first film 22. The inner surface 234 is a lower surface (negative Z-side surface) of the first film 22.

Referring to FIG. 6, the first film 22 of the present embodiment comprises two layers consisting of a meltable layer 146 which is meltable by heat-treatment and an unmeltable layer 148 which is not meltable by heat-treatment. The meltable layer 146 is located under the unmeltable layer 148. For example, the meltable layer 146 is made of polyethylene, and the unmeltable layer 148 is made of nylon. According to this structure, the meltable layer 146 can be fused to another meltable layer of another member while the unmeltable layer 148 is maintained. However, the present invention is not limited thereto. For example, the first film 22 may comprise only one layer which is the unmeltable layer 148 or may comprise three or more layers.

The first film 22 is formed with a main opening 244 and a valve opening 248. Each of the main opening 244 and the valve opening 248 of the present embodiment has a small circular shape in the XY-plane and passes through the first film 22 in the Z-direction. For example, the main opening 244 has a diameter of 0.5 mm or less. Each of the main opening 244 and the valve opening 248 as described above can be formed by a forming method such as laser irradiation. However, the present invention is not limited thereto. For example, the shape and the size in the XY-plane of each of the main opening 244 and the valve opening 248 are not specifically limited.

Referring to FIGS. 1 and 6, the first sealing member 20 of the present embodiment comprises a sub-member 26 and an air valve 28 in addition to the first film 22.

The sub-member 26 of the present embodiment is a circular, thin sheet and is bendable. The sub-member 26 comprises a thin bondable portion 262 made of resin such as polyethylene terephthalate (PET) or polyurethane (PU) and a thin conductive portion 266 made of conductor such as metal. Thus, the first sealing member 20 comprises the bondable portion 262 formed of a film and the thin film-like conductive portion 266.

For example, each of the bondable portion 262 and the conductive portion 266 of the present embodiment has a thickness of about 0.01 to 0.5 mm. The sub-member 26 is formed with a sub-opening 264. The sub-opening 264 has a small circular shape in the XY-plane. For example, the sub-opening 264 has a diameter of 0.5 mm or less. The sub-opening 264 passes through the bondable portion 262 in the Z-direction. However, the sub-opening 264 is filled with the conductive portion 266 so that no gap is left. In other words, the conductive portion 266 extends over the whole sub-opening 264 in the XY-plane and shuts the sub-opening 264. The conductive portion 266 is exposed upward and downward. In other words, the positive Z-side surface and the negative Z-side surface of the conductive portion 266 are exposed outward. Thus, the sub-member 26 is formed so as to be electrically connectable in the Z-direction.

For example, the sub-member 26 of the present embodiment can be formed as described below. First, a film having a thickness of about 0.01 to 0.5 mm is formed of resin such as PET or PU. Then, the film is formed with the sub-opening 264 having a diameter of 0.5 mm or less by a forming method such as laser irradiation. As a result, the bondable portion 262 is formed. Then, the sub-opening 264 is filled with conductive paste which is spread on one of opposite surfaces of the film by using a proper mask and a doctor blade. Then, the film is heated so that the conductive paste is hardened. Then, the sub-opening 264 is filled with conductive paste which is spread on a remaining one of the opposite surfaces of the film by using a proper mask and the doctor blade. Then, the film is heated so that the conductive paste is hardened. The conductive portion 266 is formed of the conductive paste as a result of the aforementioned twice heat-treatment.

The sub-member 26 of the present embodiment is formed as described above and has the aforementioned structure. However, the present invention is not limited thereto. For example, the conductive portion 266 may be formed by plating or by ink-jetting. The conductive portion 266 may be formed of metal foil which is laminated on an upper or lower surface of the bondable portion 262 so as to cover the whole sub-opening 264. The conductive portion 266 may partially protrude downward. Moreover, the shape and the size of the sub-member 26 are not specifically limited.

In the present embodiment, the diameter of the main opening 244 of the first film 22 is smaller than the diameter of the bondable portion 262 of the sub-member 26 but is larger than the diameter of the conductive portion 266 of the sub-member 26. The bondable portion 262 of the present embodiment is bonded on the outer surface 232 so as to surround the main opening 244 in the XY-plane. In other words, a part of the bondable portion 262 which is located around the sub-opening 264 is bonded to the first film 22 throughout its entire circumference so as to surround the main opening 244. The bondable portion 262 is firmly attached to the outer surface 232 and seals the edge of the main opening 244 in the XY-plane throughout its entire circumference. Thus, the sub-member 26 entirely shuts the main opening 244 and blocks air which might flow through the main opening 244.

The bondable portion 262 of the present embodiment is bonded on the outer surface 232 of the first film 22 by using a fixing member such as an adhesive. However, the present invention is not limited thereto. For example, referring to FIG. 6, the first film 22 may further comprises another meltable layer (not shown) which is located over the unmeltable layer 148. The bondable portion 262 may comprise a meltable layer (not shown) and an unmeltable layer (not shown). The meltable layer of the bondable portion 262 may be a lower layer of the bondable portion 262. According to the aforementioned modification, the bondable portion 262 can be bonded on the outer surface 232 of the first film 22 by fusing the meltable layer of the bondable portion 262 and the meltable layer of the first film 22 to each other.

Referring to FIGS. 3 and 4, the bondable portion 262 of the present embodiment has an outer edge in the XY-plane which is located outward of the main opening 244 in the XY-plane. Moreover, the bondable portion 262 has an inner edge in the XY-plane which is located inward of the main opening 244 in the XY-plane. Thus, the conductive portion 266 of the present embodiment is located inward of the main opening 244 in the XY-plane. The thus-arranged conductive portion 266 is vertically movable while the bondable portion 262 is resiliently deformed partially. In particular, when the bondable portion 262 is made of PU, the bondable portion 262 is resiliently deformable easily. However, the present invention is not limited thereto. For example, relationship in size in the XY-plane among the bondable portion 262, the main opening 244 and the conductive portion 266 can be variously modified as necessary.

Figure 7:
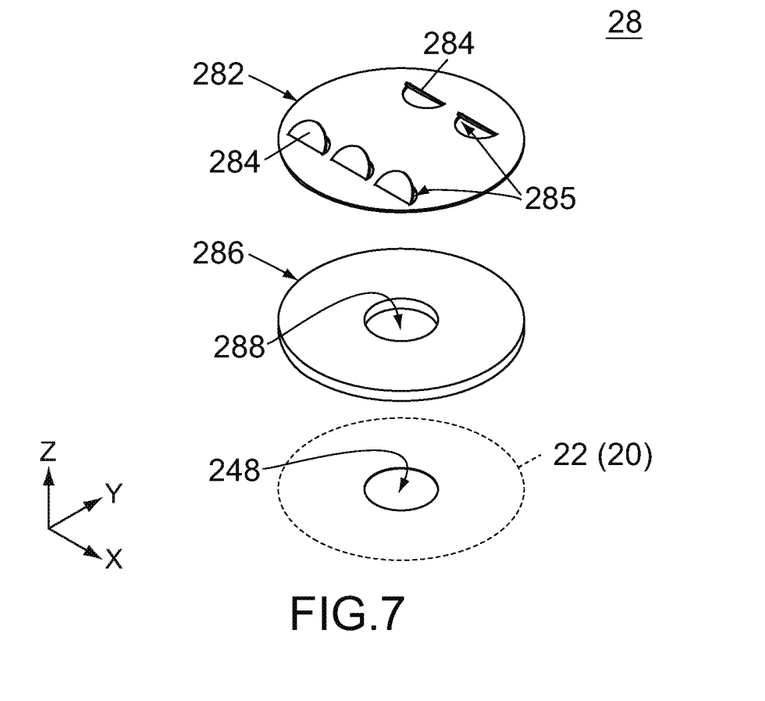
FIG. 7 is a perspective view showing the air valve of FIG. 6, wherein valves of the air valve are open.

Referring to FIGS. 6 and 7, the air valve 28 of the present embodiment comprises a cover portion 282 formed of a thin insulation film and a base portion 286 made of insulator. As shown in FIG. 7, the base portion 286 is formed with a passing hole 288. The passing hole 288 passes through the base portion 286 in the Z-direction. The cover portion 282 is formed with five valves 284 and five cuts 285 which correspond to the valves 284, respectively. Each of the cuts 285 passes through the cover portion 282 in the Z-direction. The valves 284 and the cuts 285 are located inward of an outer circumference of the cover portion 282 in the XY-plane.

Referring to FIG. 7 together with FIG. 6, the cover portion 282 is adhered to and fixed on an upper surface of the base portion 286. In particular, the outer circumference of the cover portion 282 in the XY-plane is tightly adhered to the upper surface of the base portion 286 throughout its entire circumference. In contrast, an inner part of the cover portion 282, which is located inward of the outer circumference of the cover portion 282 in the XY-plane, can be pulled away from the upper surface of the base portion 286. Thus, a passage which allows air to pass therethrough can be formed between the passing hole 288 and each of the cuts 285. The base portion 286 has a lower surface which is adhered to and fixed on the first film 22 in such a way that the passing hole 288 communicates with the valve opening 248 of the first film 22.

Referring to FIG. 1 together with FIG. 7, the air valve 28 can take either an open state shown in FIG. 7 or a closed state shown in FIG. 1. When the air valve 28 takes the open state, each of the valves 284 is apart from the corresponding cut 285. When the air valve 28 takes the closed state, each of the valves 284 completely covers the corresponding cut 285. When the air valve 28 takes the open state, an air passage via the air valve 28 is formed between the inside and the outside of the device 10. When the air valve 28 takes the closed state, the inside of the device 10 is shut off from the outside of the device 10.

As described later, the air valve 28 is used for vacuuming the inside of the device 10 upon fabrication of the device 10. The air valve 28 of the present embodiment has a structure suitable for this use. However, the present invention is not limited thereto. For example, the structure of the air valve 28 is not specifically limited, provided that the inside air of the device 10 can be discharged by using the air valve 28. Moreover, the inside of the device 10 may be vacuumed without provision of the air valve 28. In other words, the air valve 28 may be provided as necessary.

Referring to FIG. 6, the second sealing member 30 of the present embodiment is formed of, as a base thereof, a second film 32 which is an insulation film. In other words, the second sealing member 30 comprises, as a base of the second sealing member 30, the second film 32 formed of a film. The second film 32 of the present embodiment is formed of material similar to that of the first film 22 and has a structure similar to that of the first film 22. For example, the second film 32 is a thin, rectangular sheet and is bendable. The second film 32 extends in parallel to the XY-plane. The second film 32 has a peripheral edge 329 in the XY-plane. However, the present invention is not limited thereto. For example, the second sealing member 30 may comprise, as a base thereof, a rigid circuit board instead of the second film 32. The rigid circuit board may have rigidity and may be hardly bent.

The second film 32 or the rigid circuit board of the present embodiment comprises, similarly to the first film 22, two layers consisting of the meltable layer 146 which is meltable by heat-treatment and the unmeltable layer 148 which is not meltable by heat-treatment. The meltable layer 146 is located over the unmeltable layer 148. According to this structure, the two meltable layers 146 of the first film 22 and the second film 32 can be fused to each other while the unmeltable layers 148 are maintained. However, the present invention is not limited thereto. Each of the first film 22 and the second film 32 may have any structure, provided that it is in accordance with a forming method of the device 10. For example, the first film 22 and the second film 32 may be bonded together by using a fixing member such as an adhesive. In this instance, each of the first film 22 and the second film 32 may comprise only one layer which is the unmeltable layer 148. Instead, each of the first film 22 and the second film 32 may comprise three or more layers.

Referring to FIGS. 2 and 6, the second sealing member 30 of the present embodiment comprises an additional film 38 formed of an insulation film in addition to the second film 32. The additional film 38 has an uneven portion 382. As described later, the uneven portion 382 is provided in order to maintain a passage which allows air to pass therethrough upon vacuuming the inside of the device 10. In detail, the uneven portion 382 is formed with a large number of projections 384. Each of the projections 384 is a projection which projects upward and is resiliently deformable. The projections 384 are uniformly and continuously formed over the entire additional film 38 in the XY-plane. According to the structure described above, a passage which allows air to pass therethrough is formed between every adjacent two of the projections 384. The shape and the size of each of the projections 384 are not specifically limited, provided that the passage which allows air to pass therethrough can be formed.

Referring to FIG. 1 together with FIG. 2, the first film 22 and the second film 32 of the present embodiment overlap with each other so that the position of the peripheral edge 229 and the position of the peripheral edge 329 are aligned with each other in the XY-plane. However, the present invention is not limited thereto. For example, the size of the first film 22 in the XY-plane and the size of the second film 32 in the XY-plane may be different from each other. The shape of each of the first film 22 and the second film 32 is not limited to be rectangular but can be modified as necessary.

Referring to FIG. 6, the first circuit member 40 of the present embodiment has a first base portion 42 and a first conductive pattern 44. The first base portion 42 of the present embodiment is a thin, rectangular sheet formed of an insulation film and is bendable. The first base portion 42 extends in parallel to the XY-plane. The first conductive pattern 44 is formed on the first base portion 42. In detail, the first conductive pattern 44 is made of conductor such as copper and is formed on a lower surface of the first base portion 42 by a forming method such as silver ink printing or etching.

The second circuit member 50 of the present embodiment has a second base portion 52 and a second conductive pattern 54. The second base portion 52 of the present embodiment is a thin, rectangular sheet formed of an insulation film and is bendable. The second base portion 52 extends in parallel to the XY-plane. The second conductive pattern 54 is formed on the second base portion 52. In detail, the second conductive pattern 54 is made of conductor such as copper and is formed on an upper surface of the second base portion 52 by a forming method such as silver ink printing or etching.

Each of the first circuit member 40 and the second circuit member 50 of the present embodiment has the aforementioned structure. However, the present invention is not limited thereto. For example, each of the first circuit member 40 and the second circuit member 50 may be provided with one or more electronic components. One of the first circuit member 40 and the second circuit member 50 may be a single electronic component. Each of the first circuit member 40 and the second circuit member 50 may be a rigid circuit board. The forming method of each of the first conductive pattern 44 and the second conductive pattern 54 is not specifically limited, provided that each of the first conductive pattern 44 and the second conductive pattern 54 is made of conductor.

Figure 5:
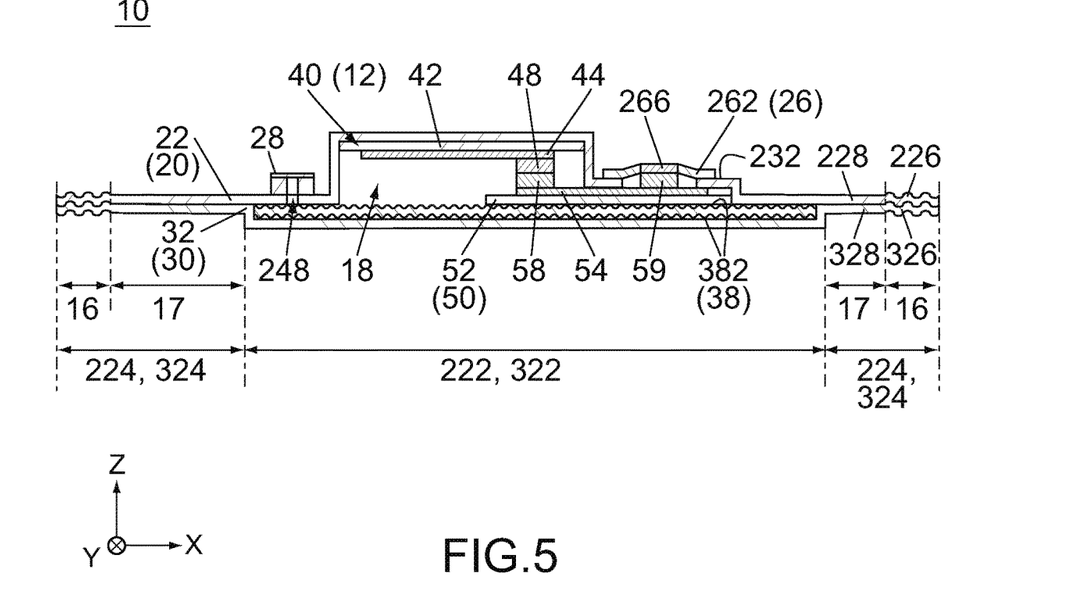
FIG. 5 is a schematic, cross-sectional view showing the device of FIG. 1, taken along line V-V, wherein an inner structure of the device is merely schematically illustrated, and the size and arrangement of each member are not equal to the actual size and arrangement thereof.

The first conductive pattern 44 of the present embodiment has a first contact point 48. The second conductive pattern 54 of the present embodiment has a second contact point 58 and an electrode 59. Thus, the first circuit member 40 comprises the first contact point 48, and the second circuit member 50 comprises the second contact point 58 and the electrode 59. Referring to FIGS. 2 and 5, the first contact point 48 and the second contact point 58 are in contact with each other in the fabricated device 10. Referring to FIG. 5, the electrode 59 and the conductive portion 266 are in contact with each other in the fabricated device 10. Thus, the first conductive pattern 44 and the second conductive pattern 54 are electrically connected with each other and are electrically connectable with a member located outside the device 10 through the conductive portion 266.

The first conductive pattern 44 and the second conductive pattern 54 illustrated in FIG. 6 are abstract conductive patterns for simple explanation about the present invention and have no specific function. In other words, even when the illustrated first contact point 48 and the illustrated second contact point 58 are brought into contact with each other, the device 10 does not work as an electronic device. For example, the actual first conductive pattern 44 and the actual second conductive pattern 54 are formed with an electronic circuit (not shown) which can measure the electric pulse of the heart of the subject. Referring to FIG. 1, this electronic circuit can obtain biological signals based on the electric pulse of the heart of the subject via the conductive portion 266.

Referring to FIG. 2, each of the number of the first contact point 48 and the number of the second contact point 58 of the present embodiment is one. Moreover, each of the number of the electrode 59 and the number of the conductive portion 266 is one. However, the present invention is not limited thereto. For example, each of the number of the first contact points 48 and the number of the second contact points 58 may be two or more. Moreover, each of the number of the electrodes 59 and the number of the conductive portions 266 may be two or more. In the fabricated device 10, the first contact points 48 should be in contact with the second contact points 58, respectively, and the electrodes 59 should be in contact with the conductive portions 266, respectively.

Hereafter, more specific explanation will be made about the device 10 of the present embodiment.

Referring to FIGS. 1 and 2, the first film 22 of the present embodiment has a first inner portion 222 and a first outer portion 224. The first outer portion 224 of the present embodiment has a first seal portion 226 and a first contact portion 228. The first inner portion 222 is located inward of the first outer portion 224 in the XY-plane. In other words, the first outer portion 224 is a part of the first film 22 which surrounds the first inner portion 222.

Referring to FIG. 2, the second film 32 of the present embodiment has a second inner portion 322 and a second outer portion 324. The second outer portion 324 of the present embodiment has a second seal portion 326 and a second contact portion 328. The second inner portion 322 is located inward of the second outer portion 324 in the XY-plane. In other words, the second outer portion 324 is a part of the second film 32 which surrounds the second inner portion 322.

Referring to FIGS. 1 and 2, the first inner portion 222 of the first film 22 and the second inner portion 322 of the second film 32 of the device 10 are parts for accommodating the circuit structure 12 and are apart from each other. The first seal portion 226 and the second seal portion 326 of the present embodiment are bonded together to form a seal trace 16. According to the present embodiment, the first seal portion 226 and the second seal portion 326 are bonded together by heat-sealing. Thus, the seal trace 16 of the present embodiment is a trace where the first seal portion 226 and the second seal portion 326 are welded to each other by heat-treatment. However, the present invention is not limited thereto, but the first seal portion 226 and the second seal portion 326 can be bonded together by various methods such as high frequency, ultrasonic, laser or adhesive.

The seal trace 16 of the present embodiment is formed throughout entire circumference of the first seal portion 226 and the second seal portion 326. The seal trace 16 surrounds the first contact portion 228 and the second contact portion 328 throughout their entire circumference in the XY-plane. However, the present invention is not limited thereto, but the seal trace 16 may be formed on a necessary part in accordance with the forming method of the device 10. For example, the seal trace 16 may be partially formed or may not be formed at all.

Referring to FIG. 5, as described later, the inside of the device 10 is vacuumed after the first seal portion 226 and the second seal portion 326 are bonded together. According to the present embodiment, upon vacuuming, the first contact portion 228 and the second contact portion 328 are brought into contact with each other in a contact region 17 because of air pressure difference. As a result, the device 10 is formed with a closed space 18. The closed space 18 is enclosed by the first inner portion 222 and the second inner portion 322. The contact region 17 of the present embodiment seamlessly surrounds the first inner portion 222 and the second inner portion 322 throughout their entire circumference in the XY-plane. However, the present invention is not limited thereto, but the contact region 17 may be formed on a necessary part in accordance with the forming method of the device 10. For example, the contact region 17 may be partially formed or may not be formed at all.

The closed space 18, which is formed as described above, is enclosed by the first sealing member 20 and the second sealing member 30 and is shut off from an outer space outside the device 10. According to the present embodiment, the first seal portion 226 and the second seal portion 326 are firmly bonded together. In addition, the contact region 17 is located inward of the seal trace 16 in the XY-plane and blocks air which might flow between the inside and the outside of the closed space 18. Thus, air pressure in the closed space 18 is kept to low pressure lower than the atmospheric pressure.

The first circuit member 40 and the second circuit member 50 are shut in the closed space 18 which is kept to the aforementioned low pressure. The first contact point 48 and the second contact point 58 are pressed against each other to be in contact with each other in the closed space 18. In detail, a contact force is generated between the first contact point 48 and the second contact point 58 because of air pressure difference between the inside and the outside of the closed space 18. The first contact point 48 and the second contact point 58 are pressed against each other because of this air pressure difference. Therefore, the contact between the first contact point 48 and the second contact point 58 can be securely kept.

Summarizing the explanation described above, the first sealing member 20 and the second sealing member 30 of the device 10 of the present embodiment overlap with each other to be in contact with each other while the first circuit member 40 and the second circuit member 50 (hereafter, simply referred to as "circuit members") are sandwiched therebetween. Each of the first sealing member 20 and the second sealing member 30 of the present embodiment is basically formed of a film.

Moreover, the structure of each of the circuit members is not restricted except that the circuit members should be provided with the electrode 59 and the contact points consisting of the first contact point 48 and the second contact point 58. Thus, each of the circuit members of the present embodiment has a simple structure and can be formed of various material. For example, the circuit members may be two insulation films formed with the conductive patterns consisting of the first conductive pattern 44 and the second conductive pattern 54. The conductive patterns may merely have the contact points and the electrode 59. In this instance, the thickness of the entire device 10 can be made extremely thin. Thus, the present embodiment provides the device 10 which is new and can be made thinner.

According to the present embodiment, the first seal portion 226 and the second seal portion 326 are bonded together, and the first contact portion 228 and the second contact portion 328 are in contact with each other. According to this structure, the closed space 18 can be reliably kept airtight. However, the present invention is not limited to the present embodiment. For example, the first seal portion 226 and the second seal portion 326 may partially surround the first contact portion 228 and the second contact portion 328 in the XY-plane. The first seal portion 226 and the second seal portion 326 may partially surround the first inner portion 222 and the second inner portion 322 in the XY-plane.

According to the present embodiment, the first circuit member 40 and the second circuit member 50 can be easily taken out from the closed space 18 by cutting off the first seal portion 226 and the second seal portion 326. Thus, according to the present embodiment, the members can be easily collected separately and can be reused.

The conductive portion 266 of the present embodiment is in contact with the electrode 59 in the closed space 18 and is partially exposed to the outer space located outside the device 10. In detail, the outer surface 232 of the first film 22 is located outside the closed space 18. The bondable portion 262 of the sub-member 26 is bonded on the thus-arranged outer surface 232. The conductive portion 266 and the electrode 59 are pressed against each other because of air pressure difference between the inside and the outside of the closed space 18 so that the contact between the conductive portion 266 and the electrode 59 can be reliably kept.

If the conductive portion 266 as described above is not provided, electronic circuits (not shown) formed in the first conductive pattern 44 and the second conductive pattern 54 should obtain biological signals of a subject with no contact with the subject. For example, the electronic circuits should obtain biological signals of the subject by contactless communication. However, weak biological signals are difficult to be accurately obtained by contactless communication. In contrast, according to the present embodiment, biological signals can be accurately obtained via the conductive portion 266 which is in contact with a skin of the subject.

Each of the first sealing member 20 and the second sealing member 30 is preferred to have a high barrier property against oxygen. More specifically, each of the first film 22 and the second film 32 (or rigid circuit board) is preferred to comprise a layer made of high oxygen barrier material which is material having a high barrier property against oxygen. According to this layer-structure, oxidation of the metal members of the circuit structure 12 can be reduced.

For example, the high oxygen barrier material may be linear low-density polyethylene (LLDPE). More specifically, the high oxygen barrier material may be PET/Al/PE which is formed by laminating polyethylene terephthalate, aluminum and polyethylene; ON/PE which is formed by laminating biaxially stretched nylon and polyethylene; PET/EVOH/PE which is formed by laminating polyethylene terephthalate, polyvinyl chloride and polyethylene; or may be formed by laminating a transparent high barrier film and polyethylene. The transparent high barrier film may be polyethylene terephthalate (PET) deposited with SiOx or aluminum oxide.

Each of the first sealing member 20 and the second sealing member 30 of the present embodiment is preferred to have a high barrier property against water vapor in addition to the high barrier property against oxygen. More specifically, each of the first film 22 and the second film 32 (or rigid circuit board) is preferred to comprise a layer made of high water-vapor barrier material which is material having a high barrier property against water vapor. According to this layer-structure, the circuit structure 12 can be water-proofed. For example, the high water-vapor barrier material may be material which is a sheet made of ON/PE, biaxially stretched polypropylene (OPP) or PET and is coated with polyvinylidene chloride (PVDC).

Each of the first sealing member 20 and the second sealing member 30 may have various barrier properties such as a barrier property against nitrogen in addition to the high barrier property against oxygen and the high barrier property against water vapor. Thus, each of the first sealing member 20 and the second sealing member 30 is preferred to have high barrier properties in accordance with its use.

The device 10 (see FIG. 1) of the present embodiment is formed via four steps consisting of a preparing step (STEP 1), a stacking step (STEP 2), a shutting-in step (STEP 3) and a vacuuming step (STEP 4). However, the present invention is not limited thereto, but the forming method of the device 10 can be modified as necessary. Hereafter, explanation will be made about an example of the forming method of the device 10 of the present embodiment.

Referring to FIG. 8, first, in the preparing step, the first sealing member 20, the second sealing member 30, the first circuit member 40 and the second circuit member 50 are prepared.

Then, in the stacking step, the first sealing member 20, the first circuit member 40, the second circuit member 50 and the second sealing member 30 are stacked on each other in this order from top to bottom along the Z-direction. Meanwhile, the first circuit member 40 and the second circuit member 50 are arranged so that the first contact point 48 and the second contact point 58 face each other in the Z-direction. Moreover, the conductive portion 266 and the electrode 59 are arranged so as to face each other in the Z-direction. The additional film 38 is located at the middle of second film 32 in the XY-plane. The first circuit member 40 and the second circuit member 50 are located at the middle of the additional film 38 in the XY-plane. In addition, the first film 22 and the second film 32 are arranged so that two of the meltable layers 146 (see FIG. 6) thereof face each other in the Z-direction.

Figure 9:
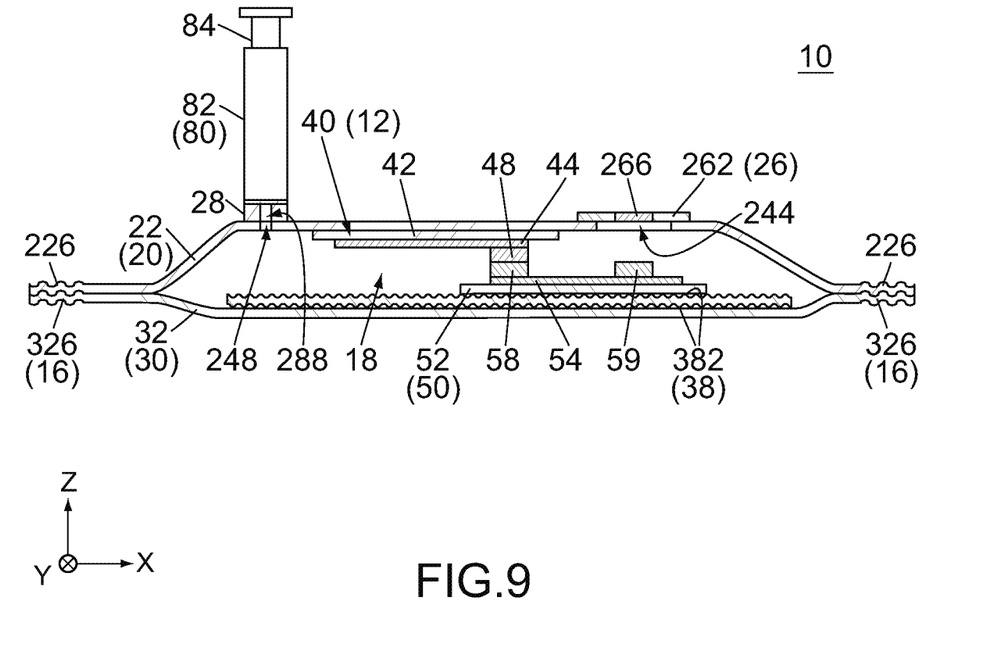
FIG. 9 is a schematic, cross-sectional view showing the device of FIG. 1, taken along line V-V, wherein the device is under manufacturing process, the inner structure of the device is merely schematically illustrated, the size and arrangement of each member are not equal to the actual size and arrangement thereof, and a side surface of an instrument for vacuuming is illustrated.

Then, in the shutting-in step, heat-sealing is applied to the first film 22 and the second film 32. In detail, parts of the two meltable layers 146, which are located at outer circumferences of the first film 22 and the second film 32 in the XY-plane, are welded to each other via heat-sealing. Referring to FIG. 9, as a result of the heat-sealing, the device 10 with the seal trace 16 is formed. The device 10 has an inner space which is enclosed by the first sealing member 20 and the second sealing member 30 and which is shut off from the outside of the device 10 except for the air valve 28.

Then, in the vacuuming step, the inside of the device 10 is vacuumed. According to the present embodiment, the air valve 28 and an instrument 80 are used to discharge the air of the inside of the device 10. The instrument 80 of the present embodiment is a syringe-type piston pump. The instrument 80 comprises a syringe 82 and a plunger 84. The syringe 82 has a lower end which has a ring shape in the XY-plane. The ring shape of the syringe 82 corresponds to the outer circumference of the cover portion 282 of the air valve 28.

In the vacuuming step, first, the lower end of the syringe 82 is pressed against the upper surface of the cover portion 282. Then, the plunger 84 is pulled upward. Meanwhile, the air valve 28 takes the open state, and an air passage is formed between the inside of the device 10 and the inside of the syringe 82. The air in the inside of the device 10 is discharged into the inside of the syringe 82 through the passing hole 288 and the cuts 285 (see FIG. 7) of the air valve 28. As a result, air pressure of the inside of the device 10 is gradually lowered. When air pressure of the inside of the device 10 becomes low pressure close to that of a vacuum, the vacuuming by using the instrument 80 is stopped.

Referring to FIG. 5 together with FIG. 9, when the vacuuming is stopped, the valves 284 (see FIG. 7) of the air valve 28 cover the cuts 285 (see FIG. 7) because of air pressure difference between air pressure of the inside of the device 10 and the atmospheric pressure, and thereby the air valve 28 takes the closed state. As a result, air pressure of the inside of the device 10 is kept to low pressure. Thus, the device 10 is formed with the closed space 18 which is shut off from the outside and has the low pressure. The first contact point 48 and the second contact point 58 are pressed against each other and are brought into contact with each other because of air pressure difference between the inside and the outside of the closed space 18. The conductive portion 266 and the electrode 59 are pressed against each other and are brought into contact with each other because of the air pressure difference between the inside and the outside of the closed space 18.

The first film 22 and the second film 32 tend to be in close contact with each other upon vacuuming, and thereby tend to form a close contact part such as the contact region 17. If the additional film 38 is not provided, the close contact part of the first film 22 and the second film 32 will be formed in the closed space 18. The thus-formed close contact part might block an air passage between the air valve 28 and a contact point region where the first contact point 48 and the second contact point 58 are arranged. As a result, air pressure of a space in which the first contact point 48 and the second contact point 58 are located might be insufficiently lowered, and thereby the first contact point 48 and the second contact point 58 might be unreliably brought into contact with each other. Similarly, the conductive portion 266 and the electrode 59 might be unreliably brought into contact with each other.

In contrast, since the additional film 38 of the present embodiment is located between the first film 22 and the second film 32, direct contact between the first film 22 and the second film 32 is prevented. Moreover, since the additional film 38 has the uneven portion 382, the air passage through the air valve 28 can be kept even in a case where the first film 22 and the second film 32 are indirectly brought into contact with each other via the additional film 38. Therefore, the first contact point 48 and the second contact point 58 can be reliably brought into contact with each other. Similarly, the conductive portion 266 and the electrode 59 can be reliably brought into contact with each other.

The additional film 38 of the present embodiment is an embossed film distinct and separable from the second film 32 and is arranged on the second film 32. The uneven portion 382 is formed over upper and lower surfaces of the additional film 38. However, the present invention is not limited thereto. For example, the additional film 38 may be adhered to and fixed on an upper surface of the second film 32. The uneven portion 382 may be formed only on the upper surface of the additional film 38. The second film 32 may be embossed so as to be formed with the uneven portion 382. In this instance, the additional film 38 does not need to be provided. Thus, the second sealing member 30 may comprise only the second film 32 which has the uneven portion 382.

The additional film 38 of the present embodiment forms the second sealing member 30 together with the second film 32. However, the present invention is not limited thereto. For example, the additional film 38 may form the first sealing member 20 together with the first film 22. More specifically, the additional film 38 may be arranged under the first film 22. Moreover, the first film 22 may be embossed so as to be formed with the uneven portion 382. In this instance, the additional film 38 does not need to be provided.

According to the forming method of the present embodiment, the first contact point 48 and the second contact point 58 are securely in contact with each other without using a fixing member such as an adhesive. The conductive portion 266 and the electrode 59 are securely in contact with each other without using a fixing member such as an adhesive. Therefore, when the device 10 is no longer used, the device 10 can be disassembled merely by cutting off the first outer portion 224 and the second outer portion 324. In addition, the first circuit member 40 and the second circuit member 50 can be shut in the closed space 18 having low pressure, and thereby degradation of the metal members due to oxidation can be reduced, for example.

Referring to FIG. 9, according to the forming method of the present embodiment, the simple instrument 80 can be used for easy vacuuming. The vacuuming by the instrument 80 can be repeatedly performed. For example, even when air pressure in the closed space 18 becomes higher during use of the device 10, the instrument 80 can be used for vacuuming again. Thus, during use of the device 10, the contact force between the first contact point 48 and the second contact point 58 can be kept, and the contact force between the conductive portion 266 and the electrode 59 can be kept. However, the present invention is not limited thereto, but the forming method of the device 10 can be modified as necessary.

For example, the structure of the instrument 80 is not specifically limited, provided that it can be used for vacuuming. A nozzle may be used instead of the illustrated instrument 80. The nozzle may be inserted into and vacuum the device 10. In this instance, the air valve 28 does not need to be provided. Alternatively, a commercially available desktop vacuum packaging machine (not shown) may be used for sealing and vacuuming. Referring to FIG. 8, the members of the device 10 may be arranged in a chamber (not shown) so that vacuuming is performed simultaneously with heat-sealing. According to this forming method, the additional film 38 does not need to be provided. In addition, the other member does not need to be provided with the uneven portion 382. However, a commercially available, simple instrument such as the instrument 80 (see FIG. 9) is preferable from a viewpoint of easy fabrication of the device 10.

According to the forming method of the present embodiment, the sub-member 26 has been bonded to the first film 22 when the preparing step starts. However, the present invention is not limited thereto. For example, the sub-member 26 may be bonded to the first film 22 by fusing after the vacuuming step ends. However, the forming method of the present embodiment is preferable from a viewpoint of reliably vacuuming the inside of the device 10.

The present embodiment can be further variously modified as described below in addition to the already described modifications.

Figure 10:
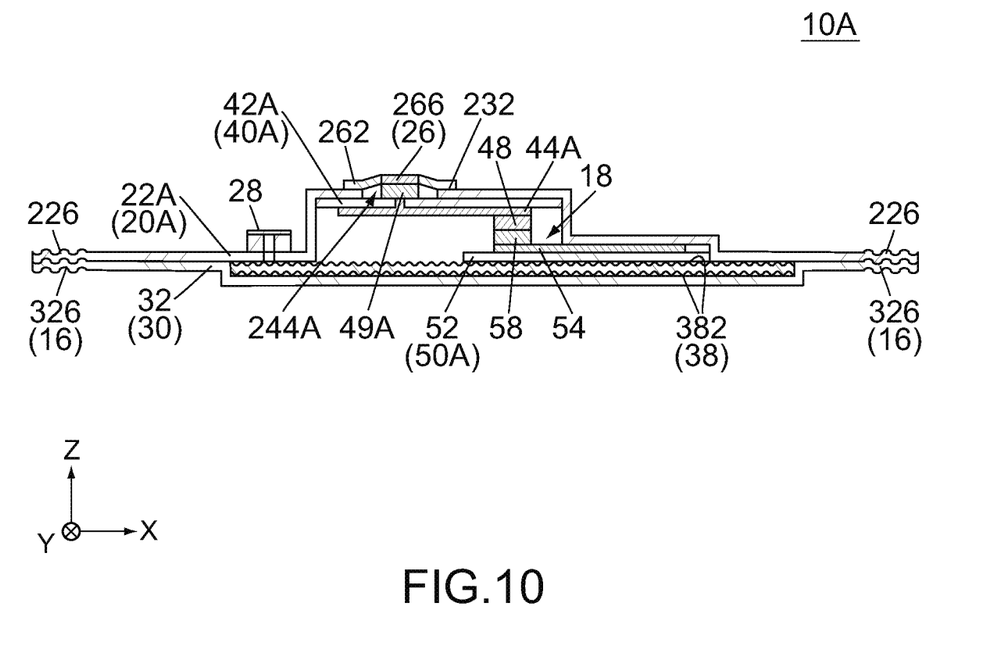
FIG. 10 is a cross-sectional view showing a modification of the device of FIG. 5, wherein an inner structure of the device is merely schematically illustrated, and the size and arrangement of each member are not equal to the actual size and arrangement thereof.

Comparing FIG. 10 with FIG. 5, a device 10A according to a first modification comprises the second sealing member 30 same as that of the device 10. Moreover, the device 10A comprises a first sealing member 20A, a first circuit member 40A and a second circuit member 50A which are different from the first sealing member 20, the first circuit member 40 and the second circuit member 50 of the device 10, respectively.

The first sealing member 20A comprises a first film 22A similar to the first film 22 and comprises the sub-member 26 and the air valve 28 same as those of the first sealing member 20. The first film 22A is formed with a main opening 244A similar to the main opening 244. The main opening 244A is located above the first circuit member 40A.

The second circuit member 50A has a structure similar to that of the second circuit member 50 except that the electrode 59 is not provided. On the other hand, the first circuit member 40A comprises an electrode 49A. In detail, the first circuit member 40A comprises a first base portion 42A and a first conductive pattern 44A. The first base portion 42A is formed with a via hole which vertically passes through the first base portion 42A. The electrode 49A is formed on an upper surface of the first base portion 42A and is connected to the first conductive pattern 44A, which is formed on a lower surface of the first base portion 42A, through the via hole. The sub-member 26 is bonded on the outer surface 232 of the first film 22A so as to shut the main opening 244A. The conductive portion 266 of the sub-member 26 is in contact with the electrode 49A the first conductive pattern 44A instead of the electrode 59 of the second conductive pattern 54.

Except for the differences described above, the device 10A has a structure similar to that of the device 10 and works similarly to the device 10. Thus, according to the present modification, the effect similar to that of the aforementioned embodiment can be obtained.

As can be seen from the explanation described above, the first circuit member 40A may comprise the electrode 49A, while the second circuit member 50 may comprise the electrode 59. Instead, the first circuit member 40A may comprise the electrode 49A, and the second circuit member 50 may comprise the electrode 59. Thus, at least one of the first circuit member and the second circuit member should comprise an electrode configured to be connected to the conductive portion 266.

Figure 11:
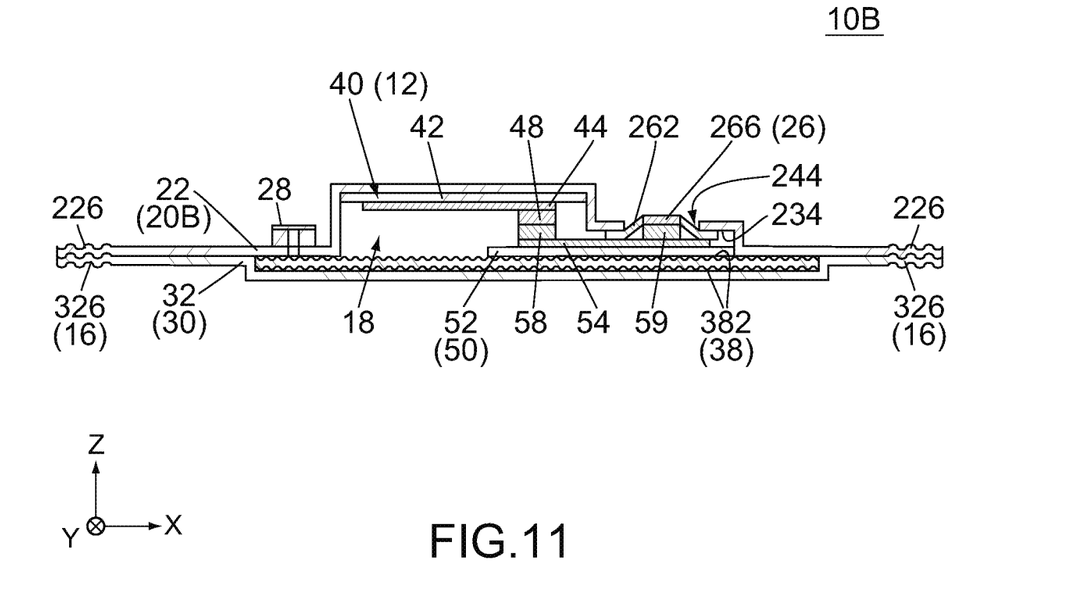
FIG. 11 is a cross-sectional view showing another modification of the device of FIG. 5, wherein an inner structure of the device is merely schematically illustrated, and the size and arrangement of each member are not equal to the actual size and arrangement thereof.

Comparing FIG. 11 with FIG. 5, a device 10B according to a second modification comprises the second sealing member 30, the first circuit member 40 and the second circuit member 50 same as those of the device 10. Moreover, the device 10B comprises a first sealing member 20B different from the first sealing member 20 of the device 10. The first sealing member 20B comprises the first film 22, the sub-member 26 and the air valve 28 same as those of the first sealing member 20. The inner surface 234 of the first film 22 is located inside the closed space 18. The bondable portion 262 of the sub-member 26 is bonded on the thus-arranged inner surface 234 by using a fixing member such as an adhesive.

Figure 12:
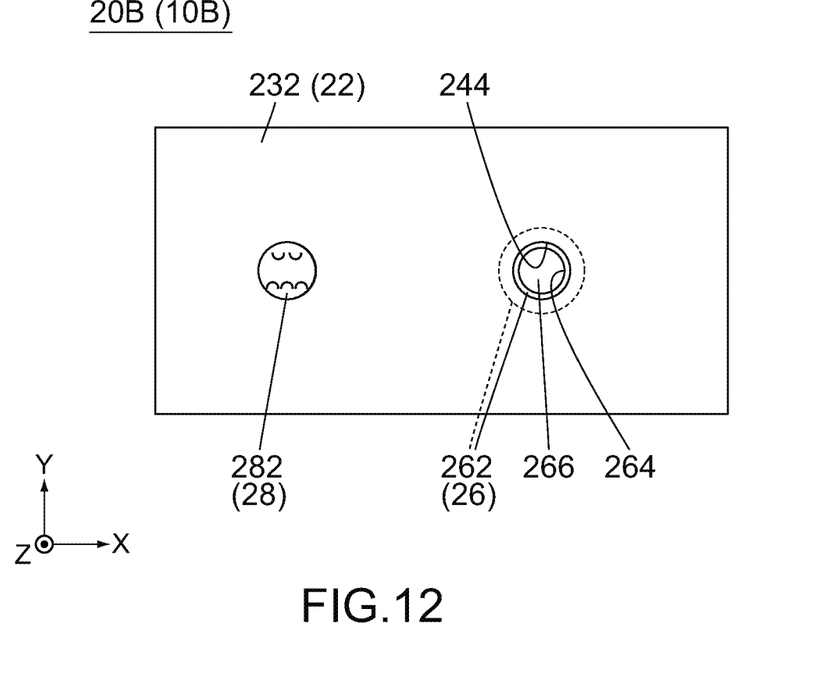
FIG. 12 is a top view showing a first sealing member of the device of FIG. 11, wherein a hidden outline of a sub-member is illustrated with dashed line.
Figure 13:
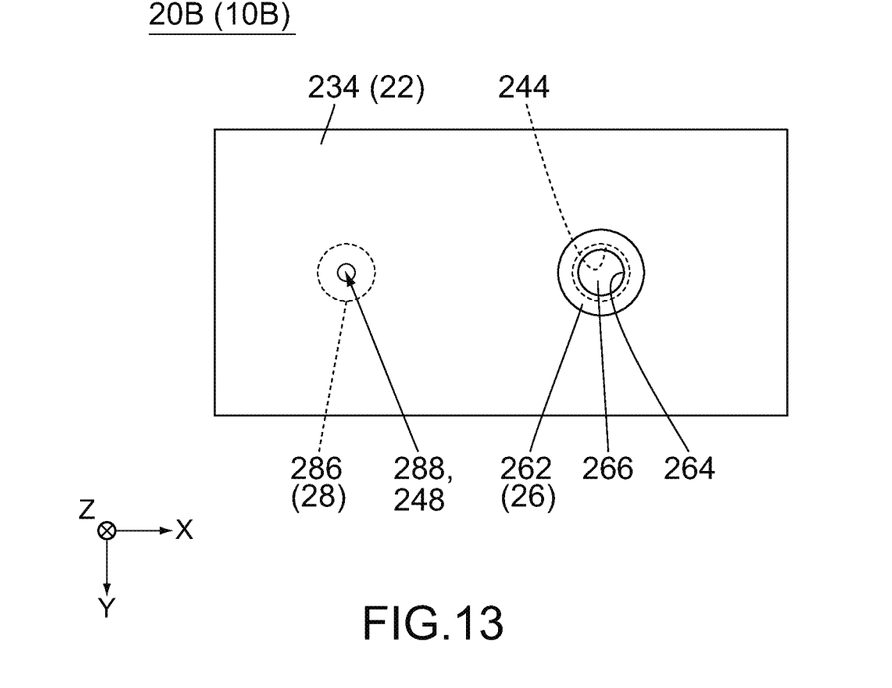
FIG. 13 is a bottom view showing the first sealing member of FIG. 12, wherein an outline of a hidden main opening of a first film and an outline of the hidden air valve are illustrated with dashed line.

Except for the differences described above, the device 10B has a structure similar to that of the device 10 and works similarly to the device 10. For example, referring FIGS. 11 to 13, a part of the bondable portion 262 which is located around the sub-opening 264 is bonded to the first film 22 throughout its entire circumference so as to surround the main opening 244. The conductive portion 266 is in contact with the electrode 59 in the closed space 18 and is partially exposed to the outer space located outside the device 10. The conductive portion 266 and the electrode 59 are pressed against each other because of air pressure difference between the inside and the outside of the closed space 18, and thereby the contact between the conductive portion 266 and the electrode 59 can be securely kept. Thus, according to the present modification, the effect similar to that of the aforementioned embodiment and the first modification can be obtained.

The bondable portion 262 of the present modification may comprise a meltable layer (not shown) and an unmeltable layer (not shown). The meltable layer of the bondable portion 262 may be an upper layer of the bondable portion 262. In this instance, the bondable portion 262 may be fused to the meltable layer 146 (see FIG. 6) of the first film 22.

Figure 14:
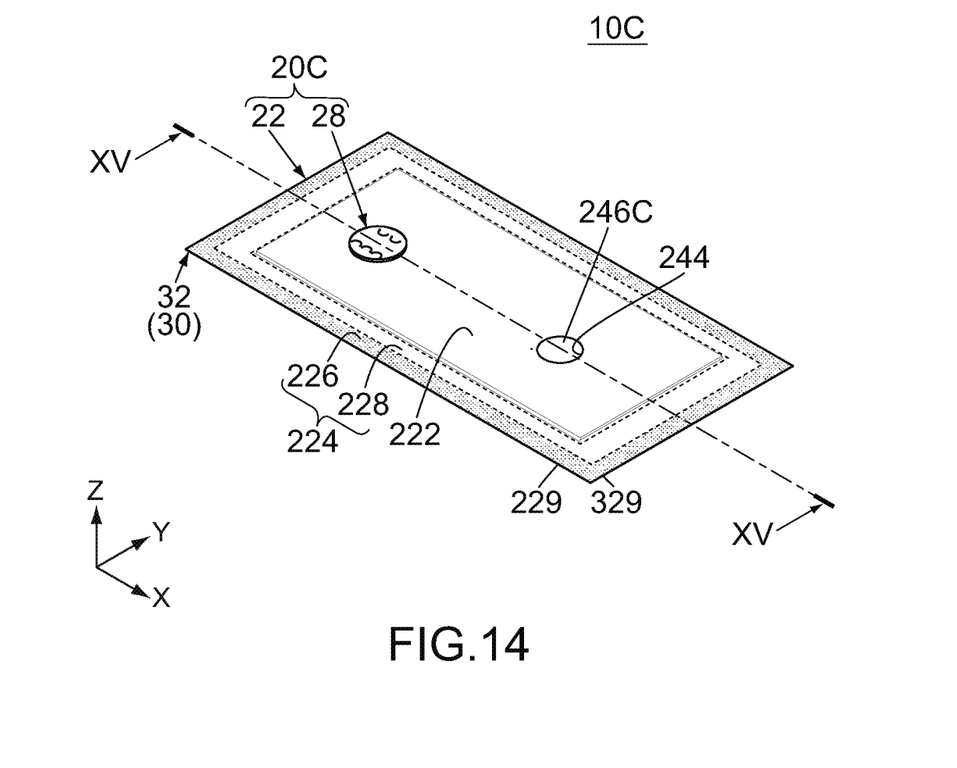
FIG. 14 is a perspective view showing a modification of the device of FIG. 1, wherein boundary lines of a contact region formed between a first sealing member and a second sealing member are illustrated with dashed line.
Figure 15:
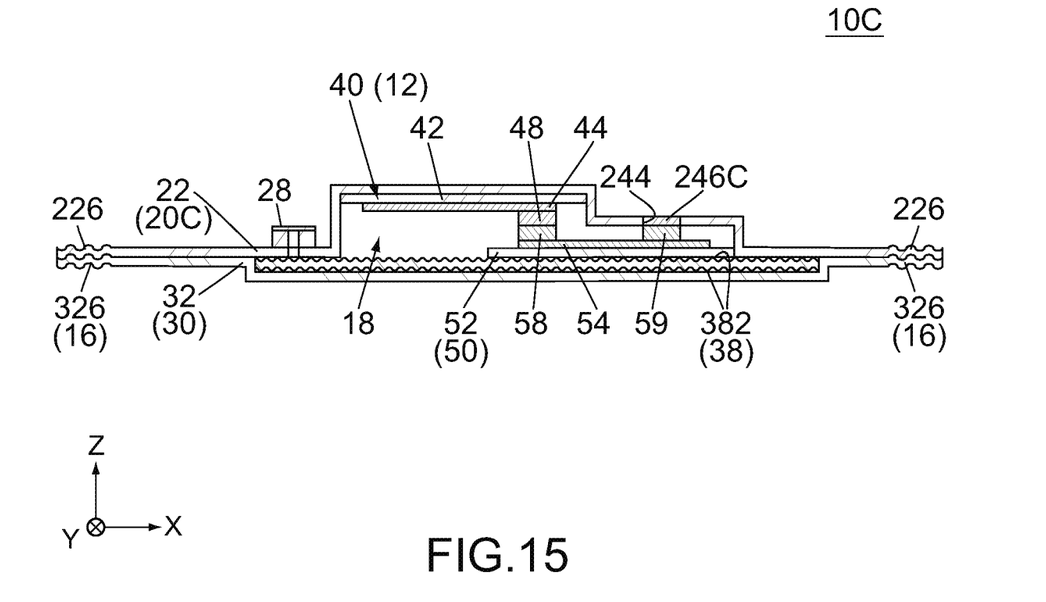
FIG. 15 is a schematic, cross-sectional view showing the device of FIG. 14, taken along line XV-XV, wherein an inner structure of the device is merely schematically illustrated, and the size and arrangement of each member are not equal to the actual size and arrangement thereof.

Comparing FIGS. 14 and 15 with FIGS. 1 and 5, a device 10C according to a third modification comprises the second sealing member 30, the first circuit member 40 and the second circuit member 50 same as those of the device 10. Moreover, the device 10C comprises a first sealing member 20C different from the first sealing member 20 of the device 10. The first sealing member 20C comprises the first film 22 and the air valve 28 same as those of the first sealing member 20. However, the first sealing member 20C does not comprise the sub-member 26. The first sealing member 20C comprises a conductive portion 246C instead of the conductive portion 266 of the sub-member 26.

The conductive portion 246C is made of conductor such as metal similarly to the conductive portion 266 and is formed by a forming method similar to that of the conductive portion 266. The conductive portion 246C shuts the main opening 244 of the first film 22. The conductive portion 246C extends over the whole main opening 244 in the XY-plane and entirely shuts the main opening 244. Thus, the conductive portion 246C blocks air which might flow through the main opening 244.

Except for the differences described above, the device 10C has a structure similar to that of the device 10 and works similarly to the device 10. For example, referring FIG. 15, the conductive portion 246C is in contact with the electrode 59 in the closed space 18 and is partially exposed to the outer space located outside the device 10. The conductive portion 246C and the electrode 59 are pressed against each other because of air pressure difference between the inside and the outside of the closed space 18, and thereby the contact between the conductive portion 246C and the electrode 59 can be securely kept. Thus, according to the present modification, the effect similar to that of the aforementioned embodiment, the first modification and the second modification can be obtained.

The present embodiment can be further variously modified in addition to the already described modifications.

For example, referring to FIG. 6, the peripheral edge 229 of the first film 22 and the peripheral edge 329 of the second film 32 may be connected to each other at a rear end (negative X-side end) thereof in a front-rear direction (X-direction). In other words, each of the first film 22 and the second film 32 may be a part of a single planar sheet which is folded so that the first film 22 and the second film 32 overlap with each other. Instead, the peripheral edge 229 of the first film 22 and the peripheral edge 329 of the second film 32 may be connected to each other except for the rear end thereof. In other words, each of the first film 22 and the second film 32 may be a part of a single folder-like sheet.

The aforementioned folder-like sheet may have an openable and closable fastener which is provided on a rear end part thereof. In this instance, vacuuming may be performed under a state where the fastener is closed. Thereafter, parts of the first film 22 and the second film 32 which are located forward (positive X-side) of the fastener may be fused to each other. The part provided with the air valve 28 may be cut off after the fusing.

The first circuit member 40 may be a member integral to the first sealing member 20. The second circuit member 50 may be a member integral to the second sealing member 30. For example, the first base portion 42 may be adhered to and fixed on a lower surface of the first film 22. Instead, the first conductive pattern 44 may be formed on the lower surface of the first film 22. The second circuit member 50 may be provided on the additional film 38. For example, the second base portion 52 may be adhered to and fixed on the upper surface of the additional film 38. Instead, the second conductive pattern 54 may be formed on the upper surface of the additional film 38. Moreover, when the second sealing member 30 does not comprise the additional film 38, the second base portion 52 may be adhered to and fixed on the upper surface of the second film 32. Instead, the second conductive pattern 54 may be formed on the upper surface of the second film 32.

Figure 16:
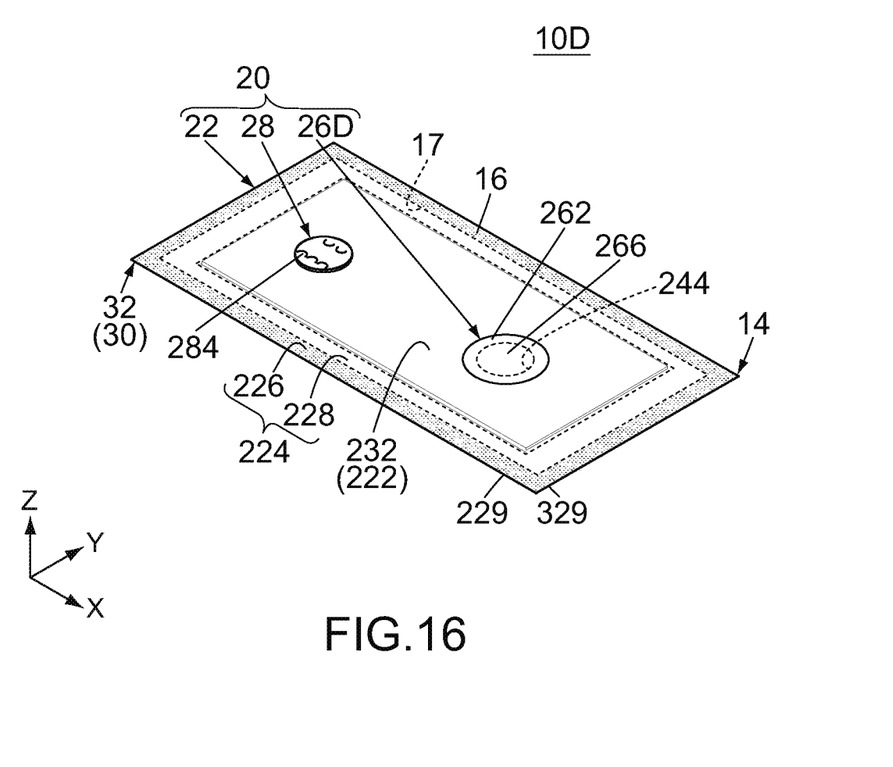
FIG. 16 is a perspective view showing another modification of the device of FIG. 1, wherein an outline of a hidden main opening of a first film and boundary lines of a contact region formed between a first sealing member and a second sealing member are illustrated with dashed line.

Referring to FIG. 16 together with FIGS. 9 to 11, as previously described, the forming method of the conductive portion 266 of the sub-member 26 is not specifically limited. For example, the sub-member 26 may be a conductive gel 26D. In other words, the first sealing member 20, 20A or 20B may comprise the conductive gel 26D (see the device 10D of FIG. 16) instead of the sub-member 26. The conductive gel 26D has flexibility and adhesiveness as well as conductivity and is thereby suitable to be directly attached to a human body. When the conductive gel 26D is used, the sub-opening 264 does not need to be formed. A part of the conductive gel 26D which covers the main opening 244 or 244A works as the conductive portion 266, and another part of the conductive gel 26D which is configured to be bonded to the first film 22 or 22A works as the bondable portion 262. Thus, the conductive gel 26D comprises the conductive portion 266 and the bondable portion 262 similarly to the sub-member 26 and works similarly to the sub-member 26.

What is claimed is:

1. A device comprising a first sealing member, a second sealing member, a first circuit member and a second circuit member, wherein:
   the first sealing member comprises, as a base of the first sealing member, a first film and a conductive portion;
   the device is formed with a closed space;
   the closed space is enclosed by the first sealing member and the second sealing member and is shut off from an outer space located outside the device;
   the first circuit member and the second circuit member are shut in the closed space;
   the first circuit member comprises a first contact point;
   the second circuit member comprises a second contact point;
   the first contact point and the second contact point are pressed against each other to be in contact with each other in the closed space because of an air pressure difference between inside and outside the closed space without using a fixing member;
   at least one of the first circuit member and the second circuit member comprises an electrode; and
   the conductive portion is in contact with the electrode in the closed space and is partially exposed to the outer space located outside the device.

2. The device as recited in claim 1, wherein:
   the first film is formed with a main opening
   the main opening passes through the first film; and
   the conductive portion shuts the main opening.

3. The device as recited in claim 1, wherein:
   the first sealing member comprises a sub-member in addition to the first film;
   the first film is formed with a main opening;
   the main opening passes through the first film;
   the sub-member comprises a bondable portion and the conductive portion;
   the sub-member is formed with a sub-opening;
   the sub-opening passes through the bondable portion;
   the conductive portion shuts the sub-opening; and
   a part of the bondable portion which is located around the sub-opening is bonded to the first film throughout its entire circumference.

4. The device as recited in claim 3, wherein:
   the first film has an outer surface;
   the outer surface is located outside the closed space; and
   the bondable portion is bonded on the outer surface.

5. The device as recited in claim 3, wherein:
   the first film has an inner surface;
   the inner surface is located inside the closed space; and
   the bondable portion is bonded on the inner surface.

6. The device as recited in claim 3, wherein the bondable portion of the sub-member comprises a film.

7. The device as recited in claim 1, wherein the second sealing member comprises, as a base of the second sealing member, a second film.

8. A device comprising a first sealing member, a second sealing member, a first circuit member and a second circuit member, wherein:
   the first sealing member comprises, as a base of the first sealing member, a first film and a conductive gel;
   the device is formed with a closed space;
   the closed space is enclosed by the first sealing member and the second sealing member and is shut off from an outer space located outside the device;
   the first circuit member and the second circuit member are shut in the closed space;
   the first circuit member comprises a first contact point;
   the second circuit member comprises a second contact point;
   the first contact point and the second contact point are pressed against each other to be in contact with each other in the closed space because of an air pressure difference between inside and outside the closed space without using a fixing member;
   at least one of the first circuit member and the second circuit member comprises an electrode;
   and
   the conductive gel is in contact with the electrode in the closed space and is partially exposed to the outer space located outside the device.

* * * * *